(12) United States Patent
Arimoto

(10) Patent No.: US 8,603,322 B2
(45) Date of Patent: Dec. 10, 2013

(54) METHOD FOR QUANTIFYING A CHEMICAL SUBSTANCE BY A SUBSTITUTIONAL STRIPPING VOLTAMMETRY TECHNIQUE

(75) Inventor: Satoshi Arimoto, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/599,424

(22) Filed: Aug. 30, 2012

(65) Prior Publication Data

US 2013/0008805 A1 Jan. 10, 2013

Related U.S. Application Data

(63) Continuation of application No. PCT/JP2011/006771, filed on Dec. 2, 2011.

(30) Foreign Application Priority Data

Jul. 5, 2011 (JP) ................................. 2011-148909

(51) Int. Cl.
*G01N 27/403* (2006.01)
(52) U.S. Cl.
USPC ................... 205/775; 205/777.5; 204/403.01; 204/424
(58) Field of Classification Search
USPC ............ 204/400, 402, 403.01, 434; 205/775, 205/777.5
See application file for complete search history.

(56) References Cited

U.S. PATENT DOCUMENTS

2009/0283404 A1 11/2009 Kakiuchi et al.

FOREIGN PATENT DOCUMENTS

| EP | 0 569 908 A2 | 11/1993 |
| JP | 06-027081 A | 2/1994 |
| JP | 2009-156836 A | 7/2009 |
| WO | WO-2008/032790 A1 | 3/2008 |

OTHER PUBLICATIONS

International Search Report mailed Mar. 6, 2012 issued in corresponding International Application No. PCT/JP2011/006771.

*Primary Examiner* — J. Christopher Ball
(74) *Attorney, Agent, or Firm* — McDermott Will & Emery LLP

(57) ABSTRACT

The purpose of the invention is to provide a method for accurately quantifying a chemical substance by a substitutional stripping voltammetry technique. A method is provided for quantifying a chemical substance contained in a sample solution, and the method comprises preparing a measurement system. The measurement system comprises a pair of working electrodes (a first and a second electrodes), a counter electrode, and a gel-coated electrode. This gel-coated electrode comprises an electrode surface, a stripping gel, and a protection gel, and the protection gel covers the stripping gel.

7 Claims, 6 Drawing Sheets

(Related art)

(Related art)

METHOD FOR QUANTIFYING A CHEMICAL SUBSTANCE BY A SUBSTITUTIONAL STRIPPING VOLTAMMETRY TECHNIQUE

This application is a continuation of International Application No. PCT/JP2011/006771, filed on Dec. 2, 2011, which claims priority of Japanese Application No. 2011-148909, filed on Jul. 5, 2011, the disclosure of these Applications are incorporated by reference herein.

TECHNICAL FIELD

The present invention relates to a method for quantifying a chemical substance by a substitutional stripping voltammetry technique.

BACKGROUND ART

Patent Literature 1 discloses a substitutional stripping voltammetry technique. The substitutional stripping voltammetry technique allows a chemical substance contained in a solution to be electrochemically quantified accurately.

FIG. 1 shows a measurement system for the substitutional stripping voltammetry technique disclosed in Patent Literature 1.

The system comprises a pair of comb-shaped working electrodes 1a and 1b, a stripping electrode 2, a reference electrode 3, a counter electrode 4, a solution 5, a stripping liquid 6, a salt bridge 7, an ion conductor 8, a potentiostat 9, a recorder 10, and a switch box 11.

The solution 5 contains a chemical substance to be quantified and an oxidation-reduction substance. The stripping liquid 6 contains a standard electrolyte and a supporting electrolyte.

FIG. 2 shows a sensor chip 101a employed for the substitutional stripping voltammetry technique disclosed in Patent Literature 1.

The sensor chip 101a comprises a plurality of electrodes 2 to 4 on the surface thereof. Furthermore, the container 64 covers the surface of the sensor chip 101a. The container 64 comprises a first penetrated opening 64a and a second penetrated opening 64b. The solution 5 and the stripping liquid 6 are supplied to the first penetrated opening 64a and the second penetrated opening 64b, respectively.

CITATION LIST

Patent Literature

[Patent Literature 1]
Japanese Patent Publication No. 3289059B.

SUMMARY OF INVENTION

Technical Problem

The evaporation of the stripping liquid 6 changes the concentration of the standard electrolyte. This lowers the quantification accuracy of the chemical substance.

One of the purposes of the invention is to provide a method for accurately quantifying a chemical substance by a substitutional stripping voltammetry technique.

Solution to Problem

1. A method for quantifying a chemical substance contained in a sample solution, the method comprising steps of:

(a) preparing a measurement system; wherein
the measurement system comprises a pair of working electrodes, a counter electrode, and a gel-coated electrode;
the pair of working electrodes is composed of a first working electrode and a second working electrode;
the gel-coated electrode comprises an electrode surface, a stripping gel, and a protection gel;
the electrode surface comprises silver;
the stripping gel covers the electrode surface;
the stripping gel contains a standard electrolyte and an ionic liquid;
the stripping gel contains no water;
the ionic liquid is composed of a cation and an anion;
the standard electrolyte is composed of the cation and a halide ion;
the protection gel covers the stripping gel;
the protection gel contains a hydrophobic ion liquid, however, contains neither the standard electrolyte nor water;
the gel-coated electrode, the first working electrode, the second working electrode, and the counter electrode are in contact with the sample solution; and
the sample solution contains the chemical substance and an oxidation-reduction substance or contains the chemical substance modified with the oxidation-reduction substance;

(b) applying an electric potential to the first working electrode with a potentiostat in a condition where the second working electrode is electrically connected to the gel-coated electrode, so as to generate reactions represented by the following chemical formulas (IX) to (XI), respectively, on the first working electrode, on the second working electrode, and on the electrode surface;

the first working electrode:

$$\begin{bmatrix} \text{the} \\ \text{oxidation} \\ \text{-reduction} \\ \text{substance} \end{bmatrix}^{n\oplus} \longrightarrow \begin{bmatrix} \text{the} \\ \text{oxidation} \\ \text{-reduction} \\ \text{substance} \end{bmatrix}^{(n+m)\oplus} + me^{\ominus} \quad \text{(IX)}$$

(reductant) (oxidant)

(wherein, n represents an integer, and m represents a positive integer.)

the second working electrode:

$$\begin{bmatrix} \text{the} \\ \text{oxidation} \\ \text{-reduction} \\ \text{substance} \end{bmatrix}^{(n+m)\oplus} + me^{\ominus} \longrightarrow \begin{bmatrix} \text{the} \\ \text{oxidation} \\ \text{-reduction} \\ \text{substance} \end{bmatrix}^{n\oplus} \quad \text{(X)}$$

(oxidant) (reductant)

(wherein, n represents an integer, and m represents a positive integer.)

the electrode surface $$Ag + X^{\ominus} \rightarrow AgX\downarrow + e^{\ominus} \quad \text{(XI)}$$

(wherein, X represents iodine atom, bromine atom, or chlorine atom.)

wherein the silver halide is deposited on the electrode surface;

(c) applying an electric potential to the gel-coated electrode in a condition where no electric potentials are applied to the first working electrode and the second working electrode, and measuring an amount of a current which flows through the gel-coated electrode; and (d) calculating a concentration of the oxidation-reduction substance (reductant) so as to quantify the chemical substance on the basis of the calculated amount of the current.

2. The method according to item 1, wherein
the stripping gel contains a hydrophobic ionic liquid.

3. The method according to item 2, wherein
the hydrophobic ionic liquid is composed of a cation selected from the group consisting of the following formulas I-(1) to I-(6) and an anion represented by the following formulas II-(1) or (II)-2:

[Chem. 1]

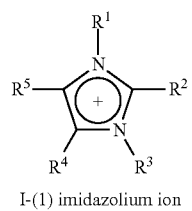

I-(1) imidazolium ion

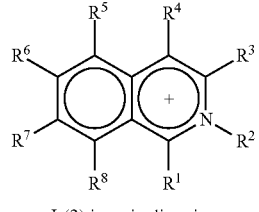 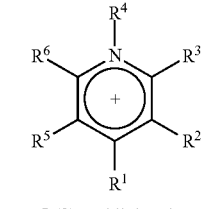

I-(2) isoquinolium ion    I-(3) pyridinium ion

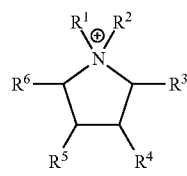 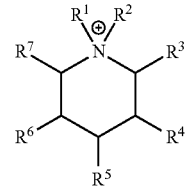

I-(4) pyrrolidinium ion    I-(5) piperidinium ion

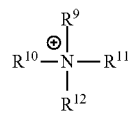

I-(6) ammonium ion (wherein, $R^1, R^2, R^3, R^4, R^5, R^6, R^7$, and $R^8$ are the same as or different from each other, and represent hydrogen atom, a straight or branched alkyl group which may contain heteroatom, an aralkyl group, or an aryl group, and $R^9, R^{10}, R^{11}$, and $R^{12}$ are the same as or different from each other, and represent a straight or branched alkyl group which may contain heteroatom, an aralkyl group, or an aryl group.)

[Chem. 2]

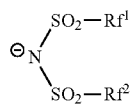

II-(1)

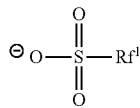

II-(2)

(wherein, $Rf^1$ and $Rf^2$ are the same as or different from each other, and represents a perfluoroalkyl group having carbon number of 1 to 4.).

4. The method according to item 1, wherein
the stripping gel contains a hydrophilic ionic liquid.

5. The method according to item 4, wherein
the hydrophilic ionic liquid is composed of a cation selected from the group consisting of the following formulas I-(1) to I-(6) and an anion represented by the following formulas III-(1) or (III)-2:

[Chem. 1]

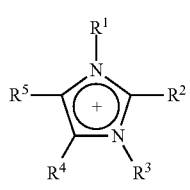 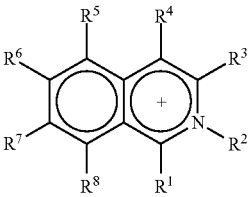

I-(1) imidazolium ion    I-(2) isoquinolium ion

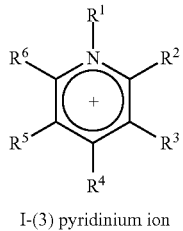 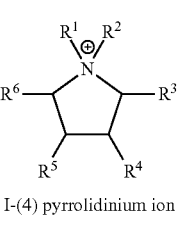

I-(3) pyridinium ion    I-(4) pyrrolidinium ion

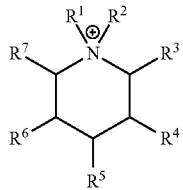

I-(5) piperidinium ion    I-(6) ammonium ion (wherein, $R^1, R^2, R^3, R^4, R^5, R^6, R^7$, and $R^8$ are the same as or different from each other, and represent hydrogen atom, a straight or branched alkyl group which may contain heteroatom, an aralkyl group, or an aryl group, and $R^9, R^{10}, R^{11}$, and $R^{12}$ are the same as or different from each other, and represent a straight or branched alkyl group which may contain heteroatom, an aralkyl group, or an aryl group.)

III-(1) tetrafluoroborate ion, and

III-(2) halide ion.

6. The method according to item 1, wherein
the standard electrolyte is composed of a cation selected from the group consisting of the following formulas I-(1) to I-(6) and a halide ion:

[Chem. 1]

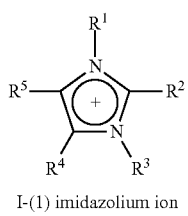

I-(1) imidazolium ion

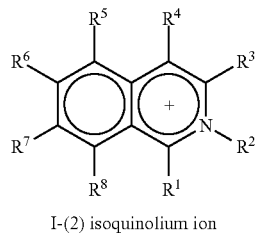

I-(2) isoquinolium ion

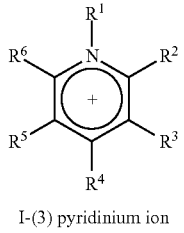

I-(3) pyridinium ion

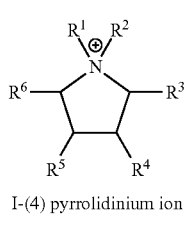

I-(4) pyrrolidinium ion

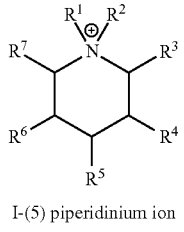

I-(5) piperidinium ion

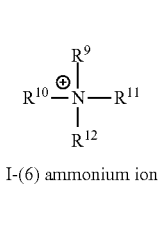

I-(6) ammonium ion (wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group.).

7. The method according to item 1, wherein the hydrophobic ion liquid contained in the protection gel is composed of a cation selected from the group consisting of the following formulas I-(1) to I-(6) and an anion represented by the following formulas II-(1) or (II)-2:

[Chem. 1]

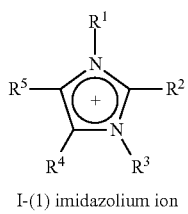

I-(1) imidazolium ion

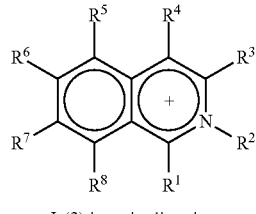

I-(2) isoquinolium ion

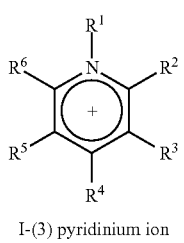

I-(3) pyridinium ion

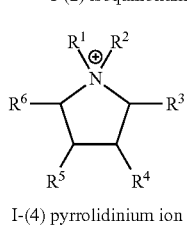

I-(4) pyrrolidinium ion

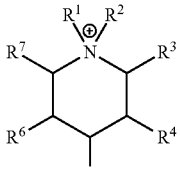

I-(5) piperidinium ion

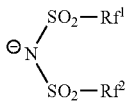

I-(6) ammonium ion (wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group.)

[Chem. 2]

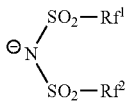

II-(1)

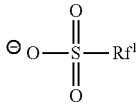

II-(2)

(wherein, $Rf^1$ and $Rf^2$ are the same as or different from each other, and represents a perfluoroalkyl group having carbon number of 1 to 4.).

Advantageous Effects of Invention

The present invention provides a method for accurately quantifying a chemical substance by a substitutional stripping voltammetry technique.

DESCRIPTION OF EMBODIMENT

An embodiment of the present invention is described below with reference to FIGS. 3 and 4.

(Step (a))

Figure 4:
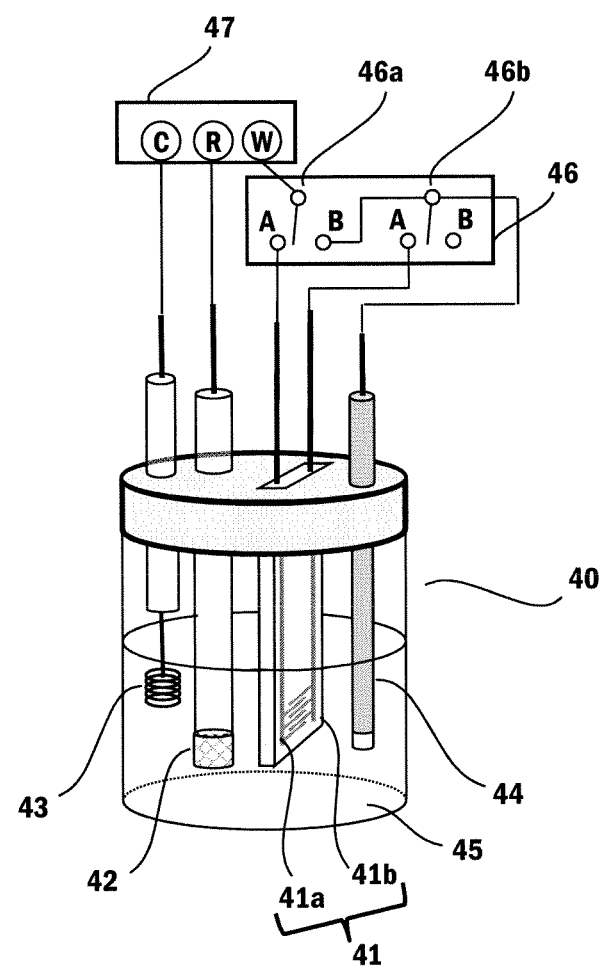
FIG. 4 shows an electrochemical cell 40 employed in the illustrative example and the comparative example.

First, a measurement system shown in FIG. 4 is prepared. FIG. 4 shows an electrochemical cell 40 employed in this example and the comparative example described later.

The measurement system comprises a pair of working electrodes 41, a counter electrode 43, and a gel-coated electrode 44. It is preferable that the measurement system further comprises a reference electrode 42.

(Working Electrodes 41)

The pair of working electrodes 41 is composed of a first working electrode 41a and a second working electrode 41b. It is preferable that the first working electrode 41a and the second working electrode 41b face each other and are engaged. In other words, it is preferable that each of the first working electrode 41a and the second working electrode 41b is comb-shaped.

As shown in FIG. 4, it is preferable that the first working electrode 41a and the second working electrode 41b are formed on a substrate.

In light of stability against electrochemical reactions, an example of the material of the first working electrode 41a and the second working electrode 41b is gold, platinum, or glassy carbon.

(Reference Electrode 42)

An example of the reference electrode 42 is a silver/silver chloride electrode.

(Counter Electrode 43)

Similarly to the pair of working electrodes 41, in light of stability against electrochemical reactions, an example of the material of the counter electrode 43 is gold, platinum, or glassy carbon.

(Gel-Coated Electrode 44)

Figure 1:
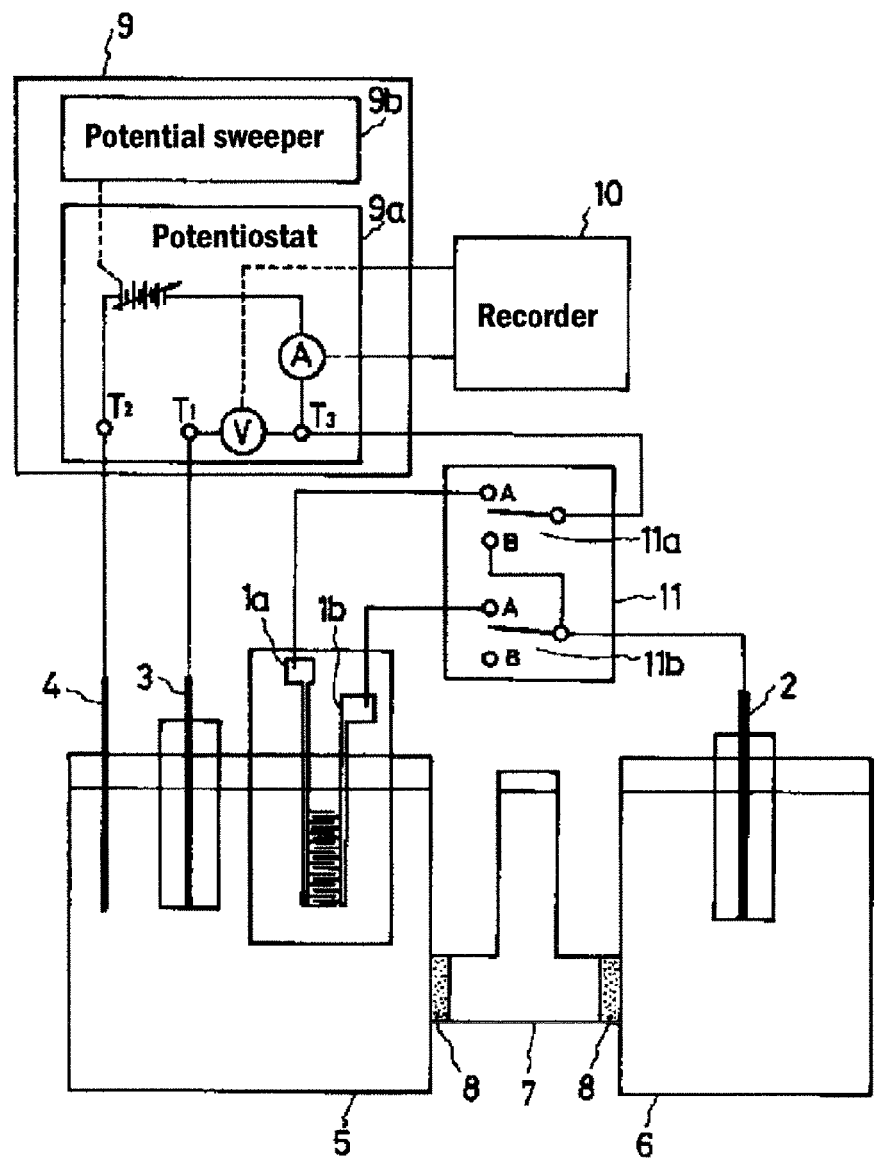
FIG. 1 shows a measurement system for the substitutional stripping voltammetry technique disclosed in Patent Literature 1.
Figure 2:
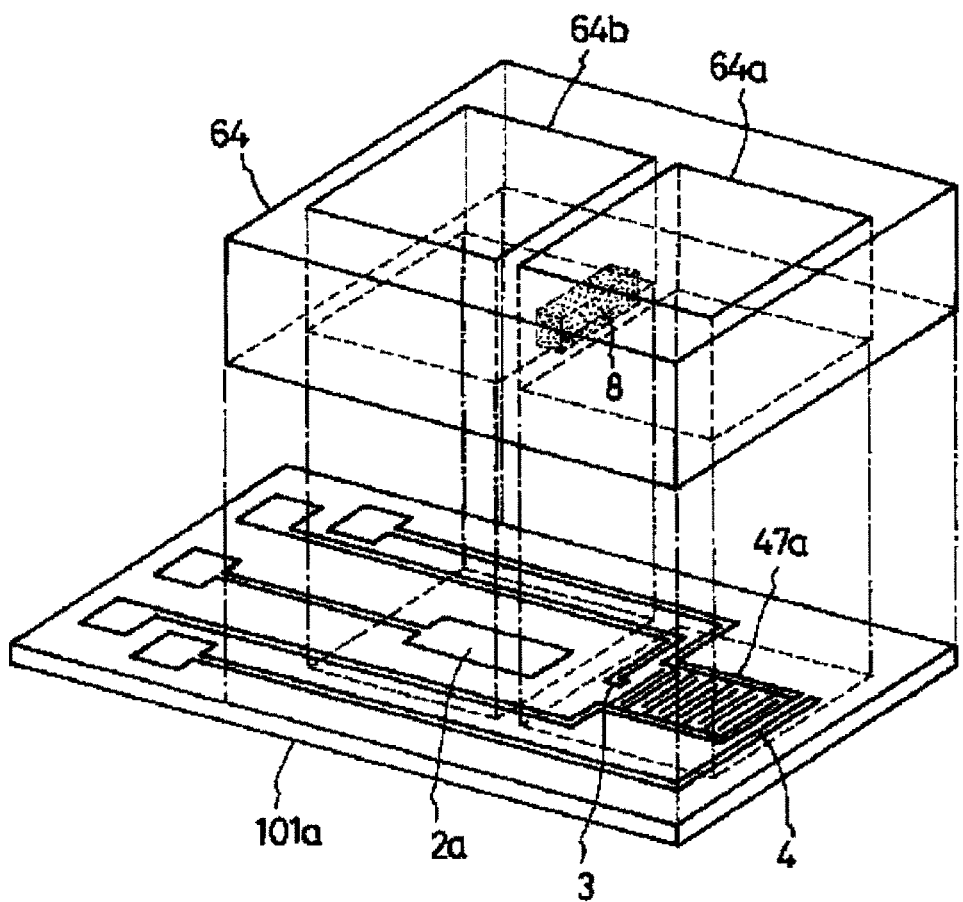
FIG. 2 shows a sensor chip for the substitutional stripping voltammetry technique disclosed in Patent Literature 1.
Figure 3A:
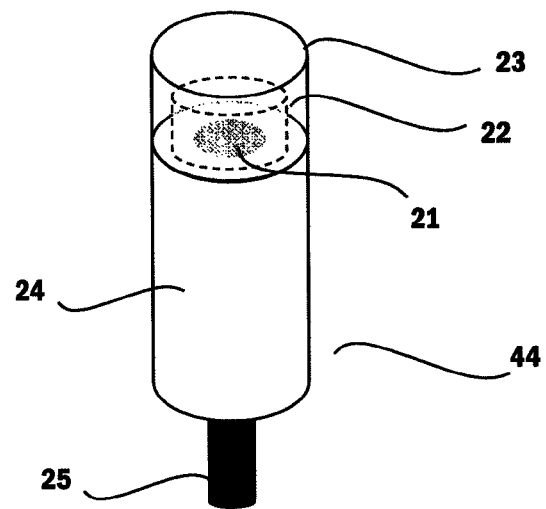
FIG. 3A shows a gel-coated electrode 44 employed in the example.

The gel-coated electrode 44 comprises an electrode surface 21, a stripping gel 22, and a protection gel 23. As shown in FIG. 3A, it is preferable that the gel-coated electrode 44 comprises them at one end of a rod-shaped insulation part 24. A lead part 25 may be provided at the other end of the rod-shaped insulation part 24. The lead part 25 is electrically connected to the electrode surface 21 through the inside of the rod-shaped insulation part 24.

(Electrode Surface 21)

The electrode surface 21 is made of silver.

(Stripping Gel 22)

The stripping gel 22 covers the electrode surface 21. The stripping gel 22 is preferably a film. The stripping gel 22 contains a standard electrolyte and an ionic liquid. The ionic liquid may be either hydrophilic or hydrophobic.

The ionic liquid serves as a supporting electrolyte.

The stripping gel 22 may be formed as below.

First, in an airtight container, hydrophobic polymer is dissolved in a solvent such as acetone with an ultrasonic wave on ice cooling to prepare an solution. An example of the hydrophobic polymer is poly (vinylidene fluoride-hexafluoropropylene), poly(methyl methacrylate), polyacrylonitrile, or polybutylacrylate.

Then, the standard electrolyte such as 1-butyl-3-methylimidazolium iodide and the ionic liquid such as 1-butyl-3-methylimidazolium bis(trifluoromethanesulfonyl)imide are added to the solution. Subsequently, the solution is stirred and then dropped on the electrode surface 21. Finally, the solvent is evaporated. In this manner, the stripping gel 22 may be formed on the electrode surface 21.

The stripping gel 22 substantially contains no water. The reason is described later.

The hydrophobic ionic liquid is composed of cation and an anion, as described in the following paragraphs. Specifically, cation is selected from Group (I). Anion is selected form Group (II).

Group (I) consists of the cations represented by the following formulas I-(1) to I-(6).

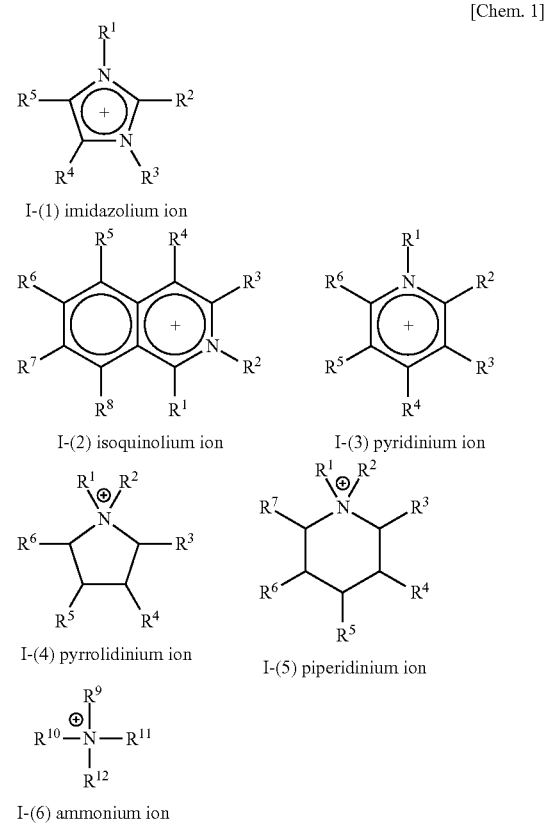

[Chem. 1]

I-(1) imidazolium ion

I-(2) isoquinolium ion

I-(3) pyridinium ion

I-(4) pyrrolidinium ion

I-(5) piperidinium ion

I-(6) ammonium ion (wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group.)

Preferably, in the imidazolium ion represented by the formula I-(1), $R^1$ is selected from the group consisting of methyl group, ethyl group, n-propyl group, isopropyl group, n-butyl group, isobutyl group, and t-butyl group, $R^2$ is a hydrogen atom or methyl group, $R^3$ is an alkyl group having carbon number of 1 to 6 which may contain hetero atom, and $R^4$ and $R^5$ are a hydrogen atom.

Preferably, in the isoquinolium ion represented by the formula I-(2), $R^2$ is an alkyl group having carbon number of 1 to 6 which may contain hetero atom, and $R^1$, $R^3$, $R^4$, $R^5$, $R^6$, $R^7$, and $R^8$ are a hydrogen atom.

Preferably, in the pyridinium ion represented by the formula I-(3), $R^1$ is an alkyl group having carbon number of 1 to 6 which may contain hetero atom, and $R^2$, $R^3$, $R^4$, $R^5$ and $R^6$ are a hydrogen atom.

Preferably, in the pyrrolidinium ion represented by the formula I-(4), $R^1$ is selected from the group consisting of methyl group, ethyl group, n-propyl group, isopropyl group, n-butyl group, isobutyl group, and t-butyl group, $R^2$ is an alkyl group having carbon number of 1 to 6 which may contain hetero atom, $R^3$, $R^4$, $R^5$, and $R^6$ are a hydrogen atom.

Preferably, in the piperidinium ion represented by the formula I-(5), $R^1$ is selected from the group consisting of methyl group, ethyl group, n-propyl group, isopropyl group, n-butyl group, isobutyl group, and t-butyl group, $R^2$ is an alkyl group having carbon number of 1 to 6 which may contain hetero atom, and $R^3$, $R^4$, $R^5$, $R^6$, and $R^7$ are hydrogen atom.

Preferably, in the ammonium ion represented by the formula I-(6), $R^9$, $R^{10}$, $R^{11}$, and $R^{12}$ are the same as or different from each other, and represent an alkyl group having carbon number of 1 to 6 which may contain halogen atom, a phenyl group, or a benzyl group.

The above described Group (II) consists of anions represented by the following formulas II-(1) and II-(2).

[Chem. 2]

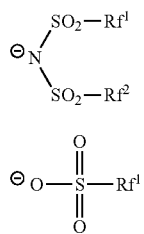

(wherein, $Rf^1$ and $Rf^2$ are the same as or different from each other, and represents a perfluoroalkyl group having carbon number of 1 to 4.)

Preferably, in the anion represented by the formula II-(1), both of $Rf^1$ and $Rf^2$ are perfluoromethyl group or perfluoroethyl group.

Preferably, in the anion represented by the formula II-(2), $Rf^1$ is trifluoromethyl group.

More specifically, an example of the material of the hydrophobic ionic liquid is described below:
1,3-Dimethylimidazolium bis(trifluoromethanesulfonyl)imide,
1-Ethyl-3-methylimidazolium bis(trifluoromethanesulfonyl)imide,
1-Ethyl-3-methylimidazolium triflate,
1-Ethyl-3-methylimidazolium bis(pentafluoroethanesulfonyl)imide,
1,3-Diethylimidazolium bis(trifluoromethanesulfonyl)imide,
1,3-Diethylimidazolium triflate,
1-Butyl-3-ethylimidazolium triflate,
1,2-Dimethyl-3-ethylimidazolium bis(trifluoromethanesulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethanesulfonyl)imide,
1,2-Dimethyl-3-propylimidazolium bis(trifluoromethanesulfonyl)imide,
N,N-Propylmethylpyrrolidinium bis(trifluoromethanesulfonyl)imide,
Propyltrimethyammonium bis(trifluoromethanesulfonyl)imide,
N,N-Methylpropylpiperidinium bis(trifluoromethanesulfonyl)imide and
N-Butylpyridinium bis(trifluoromethanesulfonyl)imide The hydrophilic ionic liquid is composed of the above-mentioned cation and the following anion. Specifically, the cation is selected from Group I. The anion is selected form Group III.

Group III consists of anions represented by III-(1) and III-(2).
III-(1): tetrafluoroborate ion, and
III-(2): halide ion.

More specifically, an example of the material of the hydrophilic ionic liquid is described below.

1-Ethyl-3-methylimidazolium tetrafluoroborate,
1-Butyl-3-methylimidazolium tetrafluoroborate,
1-Methyl-3-propylimidazolium tetrafluoroborate,
1-Butyl-3-methylimidazolium iodide,
1-Hexyl-3-methylimidazolium bromide,
1-Hexyl-3-methylimidazolium chloride,
1-Octyl-3-methylimidazolium chloride and
N-Hexylpyridinium chloride.

The standard electrolyte is composed of the above-mentioned cation and a halide ion. Specifically, the cation is selected from Group I. The halide ion denotes chloride ion, bromide ion, or iodide ion.

It is preferred that the standard electrolyte has the same cation as the ionic liquid in light of solubility. For example, when the cation of the standard electrolyte is represented by the above formula I-(1), it is preferable that the cation of the ionic liquid is also represented by the above formula I-(1). More particularly, when the ionic liquid is 1-butyl-3-methylimidazolium bis(trifluoromethanesulfonyl)imide, the standard electrolyte is preferably 1-butyl-3-methylimidazolium halide.

Next, the protection gel 23 is described below in more detail.

The protection gel 23 covers the stripping gel 22. In other words, the stripping gel 22 is interposed between the protection gel 23 and the electrode surface 21. As shown in FIG. 3A, it is preferred that the protection gel 23 covers the entire of the stripping gel 22 in such a manner that the stripping gel 22 is hidden completely by the protection gel 23.

The protection gel 23 contains the hydrophobic ionic liquid; however the protection gel 23 does not contain the standard electrolyte. The hydrophobic ionic liquid serves as a supporting electrolyte, similarly to the stripping gel 22. The protection gel 23 is formed so that the hydrophobic ionic liquid is not mixed with the sample solution.

The protection gel 23 may be formed as below.

Similarly to the case of the stripping gel 22, in an airtight container, the hydrophobic polymer such as poly (vinylidene fluoride-hexafluoropropylene) is dissolved in a solvent such as acetone with an ultrasonic wave on ice cooling to prepare a solution. A hydrophobic ionic liquid such as 1-butyl-3-methylimidazolium bis(trifluoromethanesulfonyl)imide is added to the solution. Subsequently, the solution is stirred and dropped on the stripping gel 22. Finally, the solvent is evaporated. Thus, the protection gel 23 is formed.

The gel-coated electrode 44, the first working electrode 41a, the second working electrode 41b, and the counter electrode 43 are in contact with the sample solution 45. More particularly, at least a part of each electrode is immersed in the sample solution 45.

The sample solution 45 contains a chemical substance to be quantified and an oxidation-reduction substance. An example of the chemical substance is an antigen, an antibody, a nucleic acid, a cell, bacteria, virus, a hapten, or sugar. In the present invention, the sample solution 45 contains the oxidation-reduction substance in the reduction condition. The chemical substance to be quantified and an oxidation-reduction substance may be distinct. For example, the chemical substance to be quantified is an enzyme, and the oxidation-reduction substance is an electric mediator such as potassium ferrocyanide. Or, the chemical substance to be quantified may be modified with the oxidation-reduction substance. An example of such a chemical substance modified with the oxidation-reduction substance is a protein modified with a ferrocenecarboxylic acid (hereinafter, "FcCOOH").

(Step (b))

After the measurement system is prepared in accordance with the step (a), the step (b) is performed.

In the step (b), an electric potential is applied to the first working electrode 41a by potentiostat 47 in a condition where the second working electrode 41b is electrically connected to the gel-coated electrode 44. More particularly, the switch 46a shown in FIG. 4 is connected to Terminal A. The switch 46b is also connected to Terminal A.

Thus, a redox cycle is formed between the pair of comb-shaped working electrodes 41.

When the oxidation-reduction substance is ferrocenecarboxylic acid, the following reactions represented by the following chemical formulas (IV) to (VI) are caused on the first working electrode 41a, the second working electrode 41b, and the gel-coated electrode 44.

Silver halide is deposited on the electrode surface 21, which is composed of silver.

Working electrode 41a:

[Chem. 4]

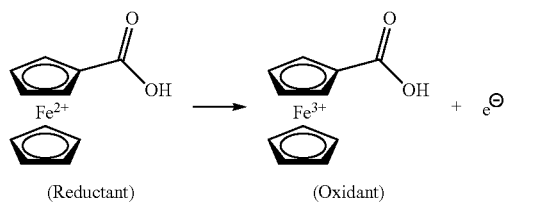

(Reductant)                (Oxidant)

Working electrode 41b:

[Chem. 5]

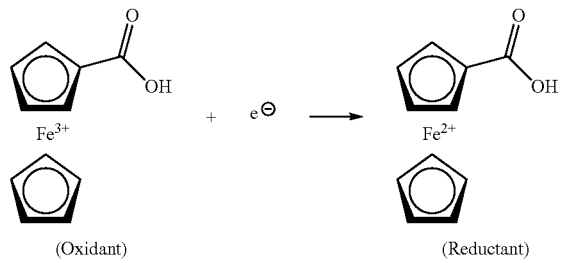

(Oxidant)                (Reductant)

Gel-coated electrode 44:

[Chem. 6]

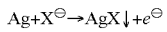 (VI)

(wherein, X represents iodine atom, bromine atom, or chlorine atom.)

(Step (c))

After the step (b), the step (c) is performed.

In the step (c), no electric potentials are applied to the first working electrode 41a and the second working electrode 41b. In this condition, an electric potential is applied to the gel-coated electrode 44. It is preferable that the gel-coated electrode 44 is swept with use of the potentiostat 47. More particularly, in FIG. 4, the switch 46a is connected to Terminal B. The switch 46b is also connected to Terminal B. As shown in the following chemical formula (VII), the silver halide which has been deposited in the step (b) is decomposed by an electric current, and the generated halide ion is dissolved in the stripping gel 22. Silver is generated on the electrode surface 21.

Gel-Coated Electrode 44:

[Chem. 7]

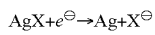 (VII)

(wherein, X represents iodine atom, bromine atom, or chlorine atom.)

In case where the stripping gel 22 contains water, the water inhibits the reaction represented by the formula (VI). This is because water has an affinity with the halide ion. Therefore, the stripping gel 22 contains no water. However, the stripping gel 22 may contain a minute amount of water, as long as the quantification accuracy is not negatively affected. Since the ionic liquid is nonvolatile, unlike prior arts, the evaporation of the stripping gel 22 is suppressed in the step (b) and in the step (c). This allows the concentration of the standard electrolyte to be maintained. As a result, the quantification of the chemical substance is allowed to be more accurate. This characterizes the present invention.

The longer the constant potential is applied in the step (b), the higher sensitivity is achieved, since the deposition amount of silver halide is increased.

(Step (d))

The amount of the current flowing on the dissolution in the step (c) is proportional to the deposited amount of the silver halide. The deposited amount of the silver halide is proportional to the product of the concentration of the oxidation-reduction substance (reductant) by the period when the potential is applied in the step (b). In other words, the following equation is satisfied.

$$\begin{pmatrix} \text{the deposition} \\ \text{amount} \\ \text{of the silver halide} \end{pmatrix} = \begin{pmatrix} \text{the concentration} \\ \text{of the oxidation-reduction} \\ \text{substance (Reductant)} \end{pmatrix} \times \begin{pmatrix} \text{the period} \\ \text{when the potential} \\ \text{is applied} \\ \text{in the step } (b) \end{pmatrix}$$ [Math. 1]

Accordingly, the concentration of the oxidation-reduction substance (reductant) is calculated from the amount of the current flowing in the step (c). The chemical substance is quantified on the basis of the concentration of the oxidation-reduction substance (reductant) thus calculated. Needless to say, similarly to a typical procedure, when the chemical substance is quantified from the current, a standard curve which has been prepared is used.

EXAMPLE

An illustrative example of the present invention is described below.

(Preparation of the Gel-Coated Electrode 44)

FIG. 3A shows a gel-coated electrode 44 employed in the example. The gel-coated electrode 44 was prepared as below.

Fifty milligrams of poly (vinylidene fluoride-hexafluoropropylene) (available from Aldrich) was dissolved in one milliliter of acetone by ultrasonic wave on ice cooling in an airtight container to prepare an acetone solution. The copolymer had an average molecular weight of 470,000.

Fifty microliters of 1-butyl-3-methylimidazolium bis(trifluoromethanesulfonyl)imide (available from TOKYO CHEMICAL INDUSTRY CO., LTD.) containing 100 mM of 1-butyl-3-methylimidazolium iodide (available from Wako Pure Chemical Industries, Ltd.) was added to the acetone solution and stirred well. Thus, a first stock solution was prepared.

Similarly to the case of the first stock solution, fifty microliters of 1-butyl-3-methylimidazolium bis(trifluoromethanesulfonyl)imide was added to the acetone solution and stirred well. Thus, a second stock solution was prepared.

Ten microliters of the first stock solution was dropped on the electrode surface 21. The electrode surface 21 was composed of a silver plate having a diameter of 3.0 millimeters. The acetone was evaporated to form the stripping gel 22 on the electrode surface 21. Next, forty microliters of the second stock solution was dropped in such a manner that the second solution covered the stripping gel 22. The acetone was evaporated to form the protection gel 23. Thus, the gel-coated electrode 44 was obtained.

(Electrochemical Measurement)

Electrochemical measurement was conducted as below.

An electrochemical measurement system was prepared as shown in FIG. 4. The electrochemical measurement system comprised a pair of comb-shaped working electrodes 41a/41b, a reference electrode 42, a counter electrode 43, a gel-coated electrode 44, a sample solution 45, a switch box 46 and a potentiostat 47. The potentiostat was available from BAS and had a trade name of ALS-660A.

The reference electrode 42 was a silver/silver chloride electrode. The counter electrode 43 was a platinum wire. The sample solution 45 was Dulbecco's Phosphate Buffered Saline (D-PBS: 7 mM NaCl, 2.7 mM KCl, 10 mM $Na_2HPO_4$, 1.8 mM $KH_2PO_4$) containing FcCOOH.

First, the switch 46a and the switch 46b were connected to the respective terminal A, and a voltage of 0.4 volts (vs. Ag/AgCl) was applied to the first working electrode 41a for 60 seconds (step (b)). Meanwhile, the second working electrode 41b was electrically connected to the gel-coated electrode 44. Silver iodide was deposited on the electrode surface 21.

Next, the switch 46a and the switch 46b were connected to the respective terminals B. The gel-coated electrode 44 was swept with use of the potentiostat 47 (step (c)). The scan range was from −0.42 volts to −0.52 volts (vs. Ag/AgCl). The scan rate was 20 mV/s.

Figure 5:
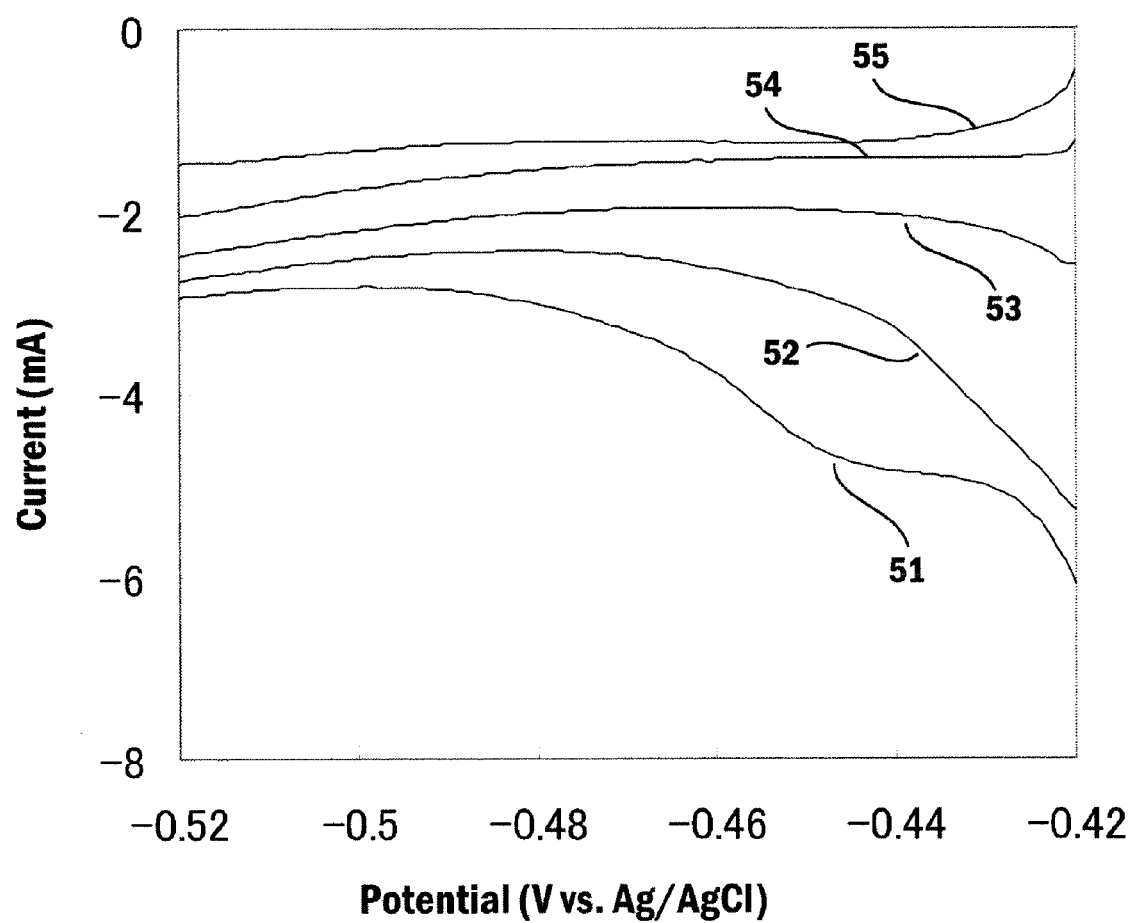
FIG. 5 shows a liner sweep voltammograms obtained in the illustrative example.

FIG. 5 shows the liner sweep voltammograms obtained in the step (c) with use of the sample solutions each containing $10^{-5}$M (reference sign: 51), $10^{-6}$M (reference sign: 52), $10^{-7}$M (reference sign: 53), $10^{-8}$M (reference sign: 54) and 0 M (reference sign: 55) of FcCOOH. The currents 51 to 54 shown in FIG. 5 mean the electrolysis of the silver iodide which had been deposited at the step (b) occurred as shown in the following chemical formula (VIII). The current was increased depending on the increase of the concentration of FcCOOH. Even the FcCOOH having a concentration of $10^{-8}$ M was detected (See current with reference number: 54).

[Chem. 8]

$$AgI + e^{\ominus} \rightarrow Ag + I^{\ominus} \qquad (VIII)$$

Comparative Example

A comparative example of the present invention is described below.

Figure 3B:
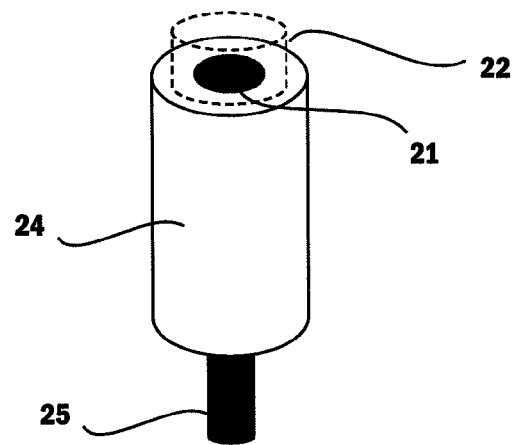
FIG. 3B shows a gel-coated electrode employed in the comparative example.

A gel-coated electrode similar to the gel-coated electrode 44 according to the example 1 was prepared except that the protection gel 23 was not formed. FIG. 3B shows the gel-coated electrode used in the comparative example. Using the gel-coated electrode, the experiment similar to the example 1 was conducted.

Figure 6:
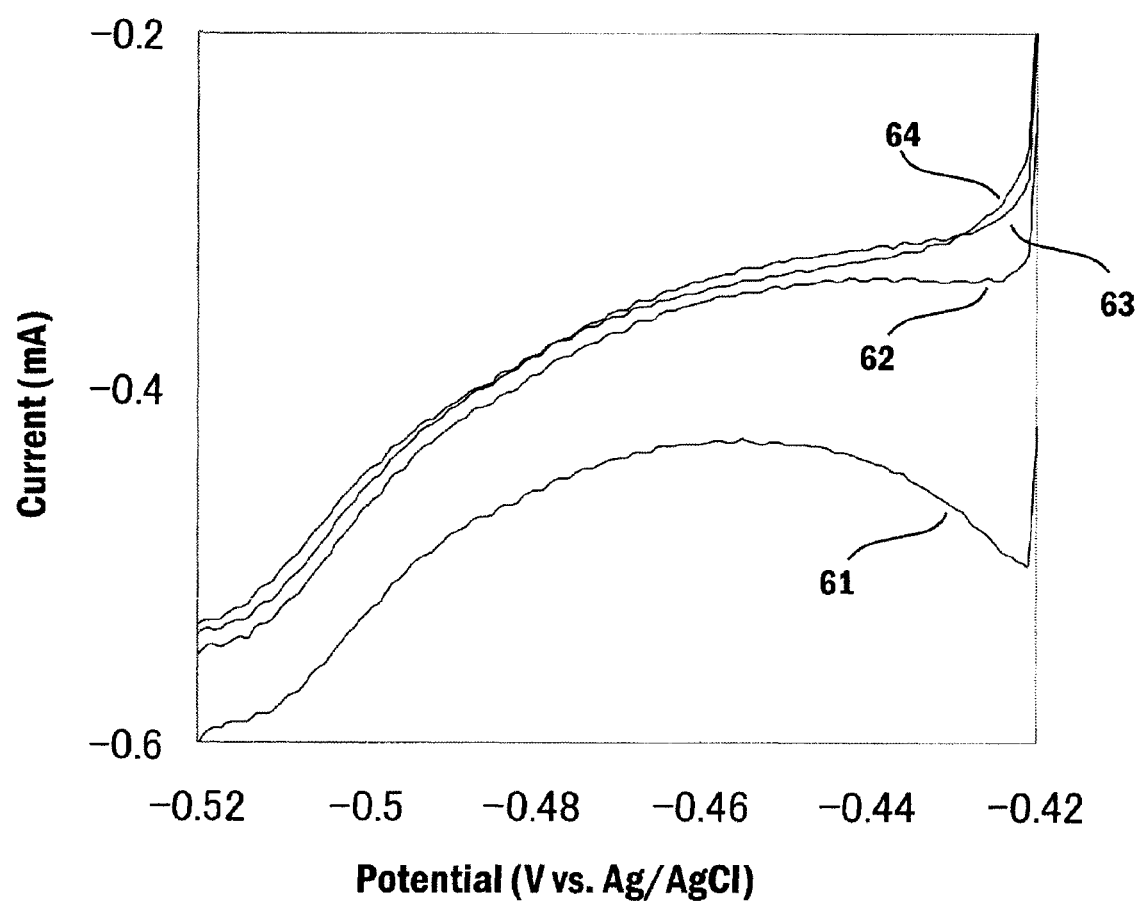
FIG. 6 shows a liner sweep voltammograms obtained in the comparative example.

FIG. 6 shows the liner sweep voltammograms obtained in the step (c) with use of the sample solutions each containing $10^{-5}$M (reference number: 61), $10^{-6}$M (reference number: 62), $10^{-7}$M (reference number: 63) and 0 M (reference number: 64) of FcCOOH. As long as the concentration of the FcCOOH is not less than $10^{-6}$ M, the reduction currents derived from the chemical formula (VIII) were observed, similarly to the case of the example. However, the FcCOOH having a concentration of $10^{-7}$M was not detected (See the current having a reference number of 63).

The stripping gel 22 did not contact directly with the sample solution because of the protection gel 23. Accordingly, the elution of the iodide ion from the stripping gel 22 was prevented. This allowed the concentration of iodide ion contained in the stripping gel 22 to be maintained constantly so as to improve the detection limit. This characterized the present invention.

INDUSTRIAL APPLICABILITY

The invention provides a method for accurately quantifying a chemical substance with a substitutional stripping voltammetry technique.

REFERENTIAL SIGNS LIST

1: Comb-shaped working electrodes
2: Stripping electrode
3: Reference electrode
4: Counter electrode
5: Solution
6: Stripping liquid
7: Salt bridge
8: Ion conductor
9: Potentiostat
10: Recorder
11: Switch box
101a: Sensor chip
2a: Stripping electrode
47a: Comb-shaped working electrodes
64: Container
21: Electrode surface
22: Stripping gel
23: Protection gel
24: Insulator
25: Lead
40: Electrochemical cell
41: Comb-shaped working electrodes
41a: First working electrode
41b: Second working electrode
42: Reference electrode
43: Counter electrode
44: Gel-coated electrode
45: Sample solution
46: Switch box
47: Potentiostat
51-55 Liner sweep voltammogram
61-64 Liner sweep voltammogram
W: Working electrode of potentiostat
R: Reference electrode of potentiostat
C: Counter electrode of potentiostat

The invention claimed is:

1. A method for quantifying a chemical substance contained in a sample solution, the method comprising steps of:
   (a) preparing a measurement system; wherein
      the measurement system comprises a pair of working electrodes, a counter electrode, and a gel-coated electrode;

the pair of working electrodes is composed of a first working electrode and a second working electrode;
the gel-coated electrode comprises an electrode surface, a stripping gel, and a protection gel;
the electrode surface comprises silver;
the stripping gel covers the electrode surface;
the stripping gel contains a standard electrolyte and an ionic liquid;
the stripping gel contains no water;
the ionic liquid is composed of a cation and an anion;
the standard electrolyte is composed of the cation and a halide ion;
the protection gel covers the stripping gel;
the protection gel contains a hydrophobic ion liquid, however, contains neither the standard electrolyte nor water;
the gel-coated electrode, the first working electrode, the second working electrode, and the counter electrode are in contact with the sample solution; and
the sample solution contains the chemical substance and an oxidation-reduction substance or contains the chemical substance modified with the oxidation-reduction substance;

(b) applying an electric potential to the first working electrode with a potentiostat in a condition where the second working electrode is electrically connected to the gel-coated electrode, so as to generate reactions represented by the following chemical formulas (IX) to (XI), respectively, on the first working electrode, on the second working electrode, and on the electrode surface;

the first working electrode:

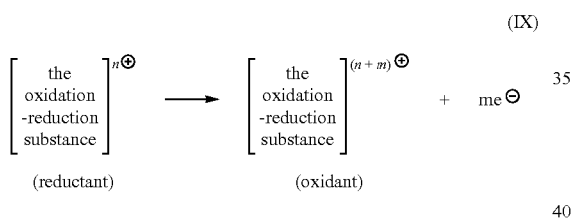

(IX)

(wherein, n represents an integer, and m represents a positive integer)

the second working electrode:

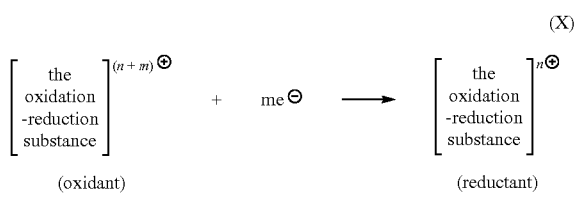

(X)

(wherein, n represents an integer, and m represents a positive integer)

the electrode surface

$Ag + X^{\ominus} \to AgX \downarrow + e^{\ominus}$ (XI)

(wherein, X represents iodine atom, bromine atom, or chlorine atom)

wherein the AgX is deposited on the electrode surface;

(c) applying an electric potential to the gel-coated electrode in a condition where no electric potentials are applied to the first working electrode and the second working electrode, and measuring an amount of a current which flows through the gel-coated electrode; and (d) calculating a concentration of the oxidation-reduction substance (reductant) so as to quantify the chemical substance on the basis of the calculated amount of the current.

2. The method according to claim 1, wherein the stripping gel contains a hydrophobic ionic liquid.

3. The method according to claim 2, wherein the hydrophobic ionic liquid is composed of a cation selected from the group consisting of the following formulas I-(1) to I-(6) and an anion represented by the following formulas II-(1) or (II)-2:

[Chem. 1]

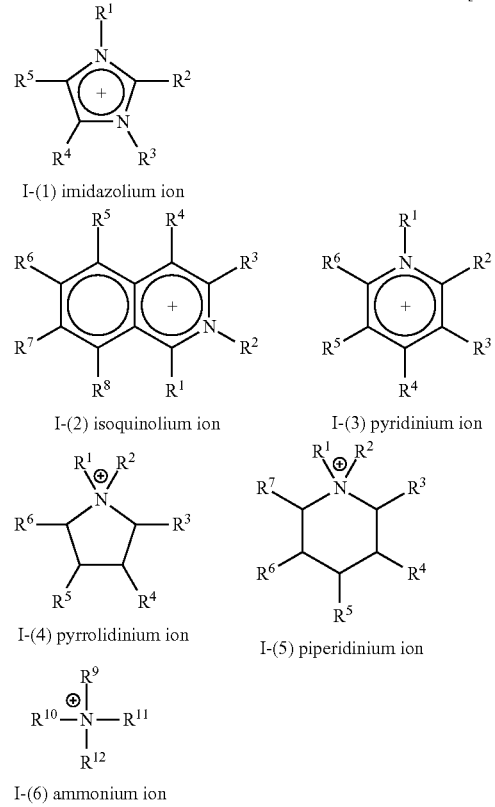

(wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group)

[Chem. 2]

(wherein, $Rf^1$ and $Rf^2$ are the same as or different from each other, and represents a perfluoroalkyl group having carbon number of 1 to 4).

4. The method according to claim 1, wherein
the stripping gel contains a hydrophilic ionic liquid.

5. The method according to claim 4, wherein
the hydrophilic ionic liquid is composed of a cation selected from the group consisting of the following formulas I-(1) to I-(6) and an anion represented by the following formulas III-(1) or (III)-2:

[Chem. 1]

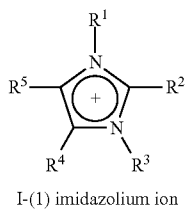
I-(1) imidazolium ion

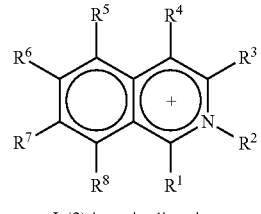
I-(2) isoquinolium ion

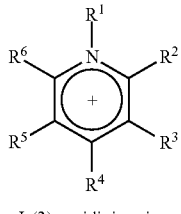
I-(3) pyridinium ion

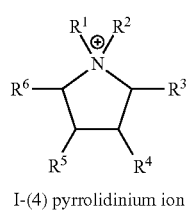
I-(4) pyrrolidinium ion

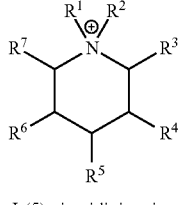
I-(5) piperidinium ion

I-(6) ammonium ion (wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group)

III-(1) tetrafluoroborate ion, and

III-(2) halide ion.

6. The method according to claim 1, wherein
the standard electrolyte is composed of a cation selected from the group consisting of the following formulas I-(1) to I-(6) and a halide ion:

[Chem. 1]

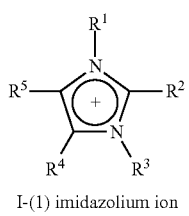
I-(1) imidazolium ion

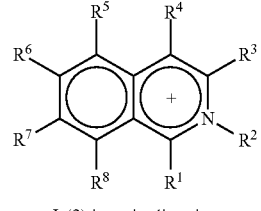
I-(2) isoquinolium ion

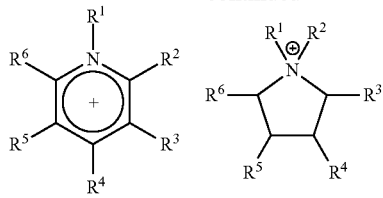
I-(3) pyridinium ion

I-(4) pyrrolidinium ion

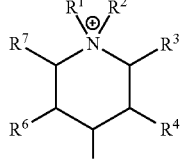
I-(5) piperidinium ion

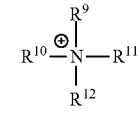
I-(6) ammonium ion (wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group).

7. The method according to claim 1, wherein
the hydrophobic ion liquid contained in the protection gel is composed of a cation selected from the group consisting of the following formulas I-(1) to I-(6) and an anion represented by the following formulas II-(1) or (II)-2:

[Chem. 1]

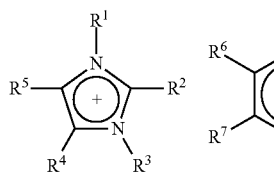
I-(1) imidazolium ion

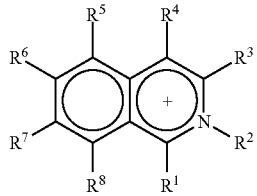
I-(2) isoquinolium ion

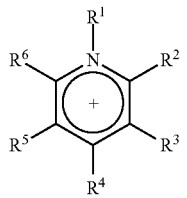
I-(3) pyridinium ion

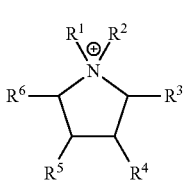
I-(4) pyrrolidinium ion

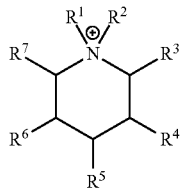
I-(5) piperidinium ion

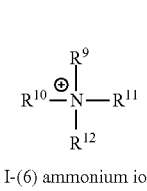
I-(6) ammonium ion (wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group)
[Chem. 2]
(wherein, $Rf^1$ and $Rf^2$ are the same as or different from each other, and represents a perfluoroalkyl group having carbon number of 1 to 4).
* * * * *